United States Patent [19]

Dinelli et al.

[11] 3,964,970

[45] June 22, 1976

[54] PROCESS FOR THE PREPARATION OF L-CARBAMYL-AMINO ACIDS AND OF THE CORRESPONDING L-AMINO ACIDS

[75] Inventors: Dino Dinelli, San Donato Milanese; Franco Morisi, San Giovanni in Persiceto; Delio Zaccardelli, Monterotondo, all of Italy

[73] Assignee: Snam Progetti S.p.A., San Donato, Milanese, Italy

[22] Filed: May 10, 1974

[21] Appl. No.: 469,019

[30] Foreign Application Priority Data
May 11, 1973 Italy .................................. 23957/73

[52] U.S. Cl. ........................................ 195/2; 195/29
[51] Int. Cl.² ............................................ C12D 13/06
[58] Field of Search .................................. 195/29, 2

[56] References Cited
UNITED STATES PATENTS 3,320,135 5/1967 Okumura et al. .................. 195/29
3,494,831 2/1970 Nakayama et al. ................. 195/29

OTHER PUBLICATIONS

Enzyme Engineering, Interscience Publishers pp. 139–141 (1972).

*Primary Examiner*—Alvin E. Tanenholtz
*Attorney, Agent, or Firm*—Ralph M. Watson

[57] ABSTRACT

A process for the preparation of only one of the two stereoisomer forms carbamyl amino acids is provided wherein certain heterocyclic compounds having an assymmetrical carbon, such as 5-substituted hydantoins, are hydrolyzed in the presence of certain enzymes, such as dihydropyrimidinase extracted from calf liver. In another embodiment of the invention, the corresponding amino acids are provided by hydrolyzing the carbamyl amino acids in the presence of these same enzymes.

23 Claims, 1 Drawing Figure

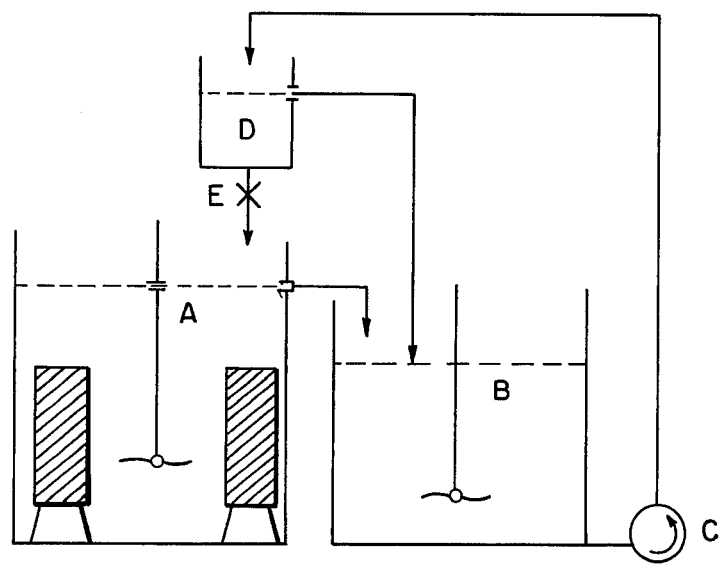

PROCESS FOR THE PREPARATION OF L-CARBAMYL-AMINO ACIDS AND OF THE CORRESPONDING L-AMINO ACIDS

It is known that natural amino acids are optically active and the spatial structure thereof is of the type generally identified by means of the letter L.

In the usual chemical syntheses of amino acids, unless asymmetrical starting compounds are used, a mixture of all possible stereoisomers wherein the D and L forms are equally distributed are obtained. The obtained mixture, called a racemic compound, is therefore optically inactive. The possibility of producing L-amino acids in a simple and economical way is a problem which has been and is very interesting, but it has not had a satisfactory solution until.

The methods, now used, are fundamentally the following three types:

I. Hydrolysis of proteins and isolation of the different amino acids. This is an expensive method because of the noble starting material, such as proteins, and because the method requires fractionating operations. Further-more this method does not allow the recovery of the amino acids destroyed by the hydrolysis.

II. Preparation of amino acids by fermentation. Presently, this method is carried out on only a few amino acids and particularly only in the production of L-glutammic acid since the costs involved allow a wide use of the product.

III. Chemical preparation of the racemic compounds and separation of the optical antipodes. The preparation of racemic compounds of many amino acids may be performed according to processes which are fundamentally very economical. However, there are difficulties in the separation of the optical antipodes and in the new utilization of the antipode D, which is not usually used as such.

The proposed separation methods are many, but, as to amino acids, a peculiar use is made of enzymes acting on derivatives of amino-acids containing substituents in the $-NH_2$ or $-COOH$ groups, above all acyl-derivatives or esters.

Substantially these methods require:

a. the treatment of the racemic amino acid with an acylating or esterifying reagent and the isolation and purification of the derivative.

b. the stereospecific action of an enzyme on the amino acid derivative.

c. the separation of L-amino acid resulting from the derivative of the D form which is not etched or vise versa (according to the enzyme stereospecificity type).

d. the treatment of the undesired antipode in order to change it into a racemic compound and let it be again fed to cycle.

All the aforesaid operations are often complex.

Frequently good results are obtained only when expensive acylating or esterifying agents are employed. The enzymes often have no absolute specificity but act on the two antipodes only through a different rate and this fact, particularly when the hydrolysis reaction of the desired antipode is protracted over a long run, causes the hydrolysis of remarkable amounts of the other antipode and then produces a product which is not pure from an optical point of view.

Moreover the transformation of the undesired antipode into a racemic compound generally requires drastic conditions and results in yields very different from the theoretical ones.

The object of the present invention is to provide a very simple and economical process for obtaining L-amino acids.

The present inventive enzymatic hydrolysis, which allows the preparation of only one stereoisomer form of an amino acid or a derivative thereof starting from a racemic compound, is promoted by the strictly selective action of the enzymes on only one of the two forms present in the racemic compound. It has been surprisingly found that several enzymes act on the racemic forms of the compounds having the formula hereinafter reported through a hydrolysis which is strictly selective as to only one of the two forms.

Enzymes within the class useful herein, include for example, those enzymes usually known for their hydrolyzing action on the simplest compounds of the hereinafter reported formula wherein no asymmetrical carbon atom exists. Other enzymes useful herein are those which are known to be able to hydrolyze one of the stereoisomer forms, but such enzymes have never before been utilized on racemic starting materials. Moreover those skilled in the art are aware that simple, experimental procedures allow the identification of the class of usual or novel enzymes which may be employed according to this invention: it is sufficient to test the behaviour thereof on a starting racemic compound.

With reference to the hereinabove discussion and for exemplification purposes of this invention it is noted that the usual enzyme named dihydropyrimidinase, prepared from calf liver according to the suggestions of Donald P. Wallach and Santiago Grisolia (J. of Biol Chem. 226 277 (1957)), hydrolyzes 4,5 dihydrouracyl, dihydrotimine and hydantoin, i.e. compounds having no asymmetrical carbon atom. Surprisingly, it has been found that if this enzyme is acted on racemic compounds (5-hydantoins), it hydrolyzes only the L form according to a strictly selective way. Similar behaviour is shown by other classes of enzymes which are known to hydrolyze only one stereoisomer form. That is, these enzymes, too, when used in presence of the racemic compound, generally confirm the property of hydrolyzing only one of the two forms present in the racemic compound according to a strictly selective way. Therefore to speak about enzymes able to strictly selectively hydrolize only one of the steroisomer forms present in the racemic compound according to the present specification is referring to all conventional or novel enzymes which, reacted on a racemic compound having the hereinafter reported formula, hydrolyze, in a strictly selective way, only one of the two forms being in the racemic compound itself. In confirmation of the aforesaid and, more particularly, with reference to the aforementioned dihydropyrimidinase, it has been surprisingly found that this enzyme, known in the hydrolysis of compounds having no asymmetrical carbon atom, is strictly selective, when used in presence of a starting racemic material, with respect to the only L form only.

The present process substantially comprises subjecting to an enzymatic hydrolysis heterocyclic compounds having an assymmetrical carbon atom, and more particularly subjecting to an enzymatic hydrolysis compounds having the formula

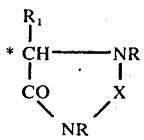

wherein X is selected from the group consisting of CO, CS and O, R is selected from the group consisting of hydrogen and simple or substituted hydrocarbon radicals having up to 8 carbon atoms, $R_1$ is a hydrocarbon radical deriving from a molecule of an amino acid wherefrom the following group has been removed

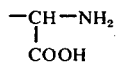

More particularly, and without be limited thereto, the inventive process, for the sake of economic and practical convenience, has the greatest interest when, in the abovesaid formula X = CO. These compounds are known as hydantoins. Even more preferred are the hydantoins containing substituents in the 5 position (hereinafter simply called 5-hydantoins). For the purpose of illustration the present process will be described with particular reference to 5-hydantoins and to the following preparations of the corresponding carbamyl amino acids and optically active amino acids. This discussion is not to be construed as a limitative of the inventive process herein which is, on the contrary, useful for the hydrolysis of the compounds having the aforedescribed formula, wherefrom the corresponding amino acids are obtained. Obviously the hydrolysis is carried out in suitable conditions of pH, temperature, concentration of the reagents, and other factors which are peculiar to the reaction being preferred.

As to the specific case of 5-hydantoins the hydrolysis is carried out by keeping the pH in the range of from 6 to 11; in fact at pH lower than 6 or higher than 11 the reaction is very slow. The hydrolisis occurs according to the scheme

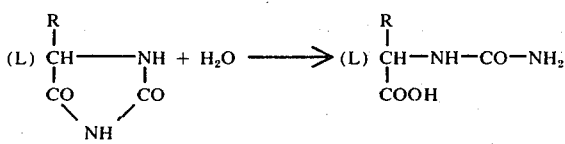

Because the (1) carbamyl-amino acid formed in the hydrolisis has an acid nature, the pH is maintained at the starting value by adding alkali during the reaction occurring. The separation of (1) carbamyl-amino acid from d-5 hydantoin, which is not hydrolyzed, may be carried out according to various methods. Very often, by cautiously and under mild stirring adding an acid amount equal to the employed alkali and cooling at 0°C, it is possible to obtain the separation of the substantially all of the (1) carbamyl-amino acid whereas S-5 hydantoin remains in solution.

It has also been found that, if the waters containing D-5 hydantoin and some (1) carbamyl-amino acid are brought to a pH higher than 7 the rotatory power decreases to a null value or even to a little opposite value, because d-5 hydantoin racemizes while (1) carbamyl-amino acid does not change.

The racemization rate of (d) - 5 - hydantoin is a function of pH and the temperature. The racemization rate increases as the temperature increases and also increases as the pH rises to values higher than 7.

Optically inactive 5-hydantoin, formed in this way, can be utilized in following operations.

Finally it has been found, which is another object of the present invention, that (1) carbamyl-amino acid, dissolved in water and heated up to boiling, decomposes according to the reaction

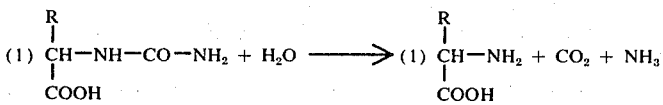

The formed amino acid can be isolated at a high optical purity degree by simply evaporating the water under vacuum.

An example will better illustrate the process.

EXAMPLE 1

1 liter of a solution containing 142 g of 5-isopropylhydantoin brought to pH of 8.0 by adding sodium hydroxide was poured into a 2 l vessel provided with a pH regulator and a stirrer. After the stirrer has been started, 10 cm³ of a solution of dihydropirimidinase obtained from calf liver were added. At the same time the pH - regulator was put in service in order to automatically allow the pH to be constant at about 8.0 by controlling the addition of a 5 N sodium hydroxide solution. In the beginning the reaction, is very fast, but decreases as (1) -5-isopropylhydantoin is consumed.

The apparatus was allowed to operate during the whole night and, as a consequence, the reaction continued until 100 cm³ of the sodium hydroxide solution were consumed. In the morning the sodium hydroxide addition was stopped and an amount of 5 N hydrochloric acid corresponding to the total amount of previously employed sodium was slowly added. Some white crystals began to form, the separation of which was completed by cooling the vessel at 0°C over some hours. By filtration and washing with 100 cm³ of frozen water, 60 – 70 g of a solid product (A) were obtained and also the washing waters (B) and the mother waters (C) which were treated separately.

The solid product (A) was constituted by moist 1-carbamyl valine containing traces of sodium chloride and protein substances. It was suspended in 200 cm³ of water and steam heated up to boiling while an equimolecular amount of HCl at 10% had being added. The product dissolved and carbon dioxide was developed. By an under vacuum evaporation, a residue was obtained consisting of (1) valine and ammonium chloride, wherefrom (1) valine was isolated according to a conventional method. The product had a rotatory power $[\alpha]_D^{20} = -28.3$ (c = 8, HCl 6 N) and a melting point of 310° – 315°C (in a closed capillary). By treating the mother waters it was further possible to obtain little amounts of the product. The washing waters (B) could be employed directly in a following operation.

The mother waters (C) had about pH of 2.5 and a remarkable rotatory power since they contain d-isopropylhydantoin. When brought to pH of 8.5–9 and kept at 35° – 40°C for 24 – 36 hours they lost the rotatory power since 5-isopropylhydantoin racemized. Then they were brought to pH of 7 by adding hydrochloric acid and evaporated under vacuum until dryness. The solid residue was treated again with water at 60°C and filtered. The solution contained, besides sodium chloride, about 70 G of 5-isopropylhydantoin and 10 – 20 g of (1) carbamylvaline as the sodium salt thereof. This solution, after the addition of 72 g of 5-isopropylhydantoin, could be used for a following operation. Our process is also more economic if use is made of the enzyme insolubilized by means of any technique employed for the enzyme insolubilization such as the techniques of chemically binding the enzymes to carriers or the technique claimed by the same applicant herein comprising englobing the enzymes in fibrous structures. These techniques permit working with solutions containing no protein and as a result the separation, the purification of the product and the recycle of the unchanged 5-hydantoin is made even easier.

EXAMPLE 2

1 liter of a solution was prepared containing
a. 500 cm$^3$ of the mother waters of the foregoing operation treated as hereinafter reported;
b. 57 g of synthetic 5-methylhydantoin;
c. distilled water and sodium hydroxide in an amount sufficient to form 1 liter of solution at pH of 8.5.

Into a small glass column, 60 cm$^3$ of a dihydropyrimidinase solution had been englobed according to the method described in Italian Pat. No. 836,462. The solution, kept at 35°C, was intaken by a pump from the vessel wherein it was passed on the fiber through the column and again sent to the vessel. The vessel was provided with stirrers and pH-regulator. The pH was kept at 8.5 by using a 5 N sodium hydroxide solution. The sodium hydroxide consumption was decreasing as the reaction was occuring and practically stopped after a total consumption of about 100 cm$^3$.

The solution was recovered in the vessel and, under weak stirring, 5 N hydrochloric acid was added at an amount corresponding to the amount of sodium hydroxide employed.

The vessel was maintained at 0°C for some hours, then crystallized l-carbamyl-alanine (A) was filtered and washed several times with 100 cm$^3$ of frozen water.

The washing waters (B) and the mother waters (C) were recovered and stored separately. l-carbamyl-alanine was dissolved in 200 cm$^3$ of water, the solution was heated up to boiling while an equimolecular amount of HCl at 10% was slowly added and then dried under vacuum. In such a way a residue was obtained constituted by l-alanine and ammonium chloride wherefrom l-alanine was isolated by conventional means.

The mother waters (C) brought at pH of 8.5, after a storage at 30–35°C for 48 hours, had practically no rotatory power. They were brought at pH of 7 with hydrochloric acid and concentrated under vacuum to a 100 cm$^3$ volume, sodium chloride being so removed. It was fltered at about 60°C and the precipitate was washed by 10 – 20 cm$^3$ of a saturated sodium chloride solution heated at 60°C. The residue on the filter was constituted by practically pure sodium chloride. The filtered product and the washing solution, joined in the washing waters (B), were added by distilled water to obtain a 500 cm$^3$ volumne and utilized in a subsequent operation.

The use of insolubilized enzymes allowed for the almost total transformation of 5-hydantoin into (1)-carbamyl-amino acids in a single operation, since it was possible to let the racemization of d-5-hydantoin occur as (1)-5-hydantoin was consumed.

EXAMPLE 3

556 g of synthetic 5-methylhydantoin were dissolved into water, then water and sodium hydroxide were added in order to obtain a 2 l volume at pH of 8.5. With reference to FIG. 1, about one half of this solution was put in a vessel (A) containing 50 g of fiber englobing dihydropyrimidinase prepared according to Example 2.

The fiber was contained in an annular basket formed by a dense mesh metallic net, also upperly shut. The vessel (A) was provided with a stirrer, pH-regulator and a weir which sent the weir treated liquid into another vessel (B) also provided with a stirrer and a pH-regulator. The vessel (B) had a bottom discharge connected to a peristaltic pump (C) which could send the liquid from the vessel (B) to the vessel (D) put above the vessel (A), also provided with a weir.

The solution, which did not enter the vessel (A), was put in the vessel (B) and brought to pH of 9.5 by sodium hydroxide.

The pump (C), the stirrers and the pH-regulator were started, one of the latter, connected to (A), kept pH of 9.5 by sodium hydroxide.

The pump (C), the stirrers and the pH-regulator were started, one of the latter, connected to (A), kept pH of 8.5 and was fed by the liquid at pH of 9.5, contained in (D) and the other one, connected to (B), kept pH of 9.5 and was fed by a 5 N sodium hydroxide solution.

The vessels (A) and (B) were kept at the temperature of 35°C.

As the reaction occurred the liquid passed from (D) to (A) wherein (1)-carbamylalanine formed and therefrom to (B) wherein, because of higher pH, d-5-methylhydantoin in excess racemizes quite fastly.

The reaction was continued until 780 cm$^3$ of 5 N NaOH were consumed, then the sodium hydroxide addition was stopped and the reaction was continued over 3-4 hours and, as a consequence, pH of the vessel (B) gradually decreased.

The whole solution was then recovered in only one vessel, whereto concentrated hydrochloric acid was slowly added under mild stirring in an amount corresponding to the total amount of the employed sodium hydroxide. (1)-carbamylalanine crystallized plentifully, and the separation thereof was promoted by cooling all the material at about 0°C and by keeping the temperature thereabout for some hours.

The crystallized product, which was separated by filtration and, washed with a small quantity water at 0°C, contained about 480 g of (1)-carbamyl-alanine containing trace amounts of water and sodium chloride impurities.

Additional amounts of product could be obtained by a suitable treatment of the mother and washing waters.

What we claim is:

1. A process for the preparation of only one of the two stereoisomer forms of carbamylamino acids comprising:

a. subjecting to hydrolysis a racemic mixture of compounds of the formula

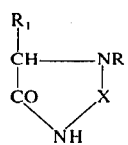

wherein X is selected from the group consisting of CO, CS and O, R is selected from the group consisting of hydrogen and hydrocarbon radicals having up to 8 carbon atoms, $R_1$ is the residue of an amino acid molecule wherefrom the

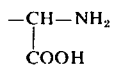

moiety has been removed, said hydrolysis being carried out in the presence of an enzyme which acts on the racemic mixture through a selective hydrolysis of only one of the optically active forms:

b. separating the sole resultant carbamyl amino acid stereoisomer.

2. The process of claim 1 further comprising the steps of:

c. racemizing the hydrolysis product remaining after said carbamyl amino acid is separated, and d. subjecting the racemic mixture resulting from step (c) to hydrolysis in the presence of an enzyme used in step (a); and e. separating the sole resultant carbamyl amino acid stereoisomer.

3. The process of claim 1 which further comprises the step of converting said carbamyl amino acid stereoisomer obtained to the corresponding amino acid.

4. The process of claim 2 which further comprises the step of converting said carbamyl amino acid stereoisomer obtained to the corresponding amino acid.

5. The process of claim 1 wherein X is CO.

6. The process of claim 2 wherein X is CO.

7. The process of claim 2 wherein said enzyme is dihydropyrimidinase extracted from calf liver.

8. The process according to claim 2 wherein X is CO; said racemizing in step (c) is carried out in an aqueous solution at a racemizing temperature and at a pH above 7.

9. The process according to claim 1 wherein said enzymes are bound to a carrier or englobed in a fibrous carrier.

10. The process according to claim 3 wherein said carbamyl amino acid is converted into the corresponding amino acid by heating said carbamyl amino acid in an aqueous solution and gradually adding thereto an equimolecular amount of an acid.

11. The process according to claim 2 wherein said racemizing of the hydrolysis product is carried out without any previous separation of the carbamyl amino acid stereoisomer.

12. The process according to claim 2 wherein said racemization is carried out simultaneously with the enzymatic hydrolysis of step (d).

13. The process according to claim 1 wherein said enzyme is dihydropyrimidinase extracted from calf liver.

14. The process of claim 11 wherein said enzyme is dihydropyrimidinase extracted from calf liver.

15. The process of claim 12 wherein said enzyme is dihydropyrimidinase extracted from calf liver.

16. The process of claim 1 wherein X is CO and said enzyme is dihydropyrimidinase extracted from calf liver.

17. The proces of claim 2 wherein X is CO and said enzyme is dihydropyrimidinase extracted from calf liver.

18. The process of claim 3 wherein X is CO and said enzyme is dihydropyrimidinase extracted from calf liver.

19. The process of claim 4 wherein X is CO and said enzyme is dihydropyrimidinase extracted from calf liver.

20. The process of claim 1 wherein X is CO; $R_1$ is methyl or isopropyl; and said enzyme is dihydropyrimidinase extracted from calf liver.

21. The process of claim 2 wherein X is CO; $R_1$ is methyl or isopropyl; and said enzyme is dihydropyrimidinase extracted from calf liver.

22. The process of claim 3 wherein X is CO; $R_1$ is methyl or isopropyl; and said enzyme is dihydropyrimidinase extracted from calf liver.

23. The process of claim 4 wherein X is CO; $R_1$ is methyl or isopropyl; and said enzyme is dihydropyrimidinase extracted from calf liver.

* * * * *